(12) United States Patent
Cagle et al.

(10) Patent No.: US 6,740,664 B2
(45) Date of Patent: *May 25, 2004

(54) METHODS FOR TREATING OTIC AND OPHTHALMIC INFECTIONS

(75) Inventors: Gerald Cagle, Forth Worth, TX (US); Robert L. Abshire, Forth Worth, TX (US); David W. Stroman, Irving, TX (US); Celeste H. McLean, Fort Worth, TX (US); Linda L. Clark, Grandview, TX (US); John M. Yanni, Burleson, TX (US)

(73) Assignee: Alcon, Inc., Hunenberg (CH)

( * ) Notice: Subject to any disclaimer, the term of this patent is extended or adjusted under 35 U.S.C. 154(b) by 8 days.

This patent is subject to a terminal disclaimer.

(21) Appl. No.: 09/887,775

(22) Filed: Jun. 22, 2001

(65) Prior Publication Data
US 2002/0022629 A1 Feb. 21, 2002

Related U.S. Application Data

(63) Continuation-in-part of application No. 09/575,850, filed on May 19, 2000, now Pat. No. 6,509,327, which is a continuation of application No. PCT/US99/22622, filed on Sep. 29, 1999, and a continuation of application No. PCT/US99/22624, filed on Sep. 29, 1999, and a continuation of application No. PCT/US99/22625, filed on Sep. 29, 1999.

(60) Provisional application No. 60/102,511, filed on Sep. 30, 1998, provisional application No. 60/102,510, filed on Sep. 30, 1998, provisional application No. 60/102,509, filed on Sep. 30, 1998, provisional application No. 60/102,508, filed on Sep. 30, 1998, provisional application No. 60/102,506, filed on Sep. 30, 1998, and provisional application No. 60/102,504, filed on Sep. 30, 1998.

(51) Int. Cl.$^7$ .............................................. A61K 31/47
(52) U.S. Cl. ...................... 514/311; 514/171; 514/912
(58) Field of Search ................................. 514/171, 311, 514/912

(56) References Cited

FOREIGN PATENT DOCUMENTS

| EP | 1 025 846 | 8/2000 |
|---|---|---|
| WO | WO 01/45679 | 6/2001 |
| WO | WO 01/89495 | 11/2001 |

*Primary Examiner*—Zohreh Fay
(74) *Attorney, Agent, or Firm*—Gregg C. Brown

(57) ABSTRACT

Ophthalmic, otic and nasal compositions containing a new class of antibiotics (e.g., moxifloxacin) are disclosed. The compositions preferably also contain one or more anti-inflammatory agents. The compositions may be utilized to treat ophthalmic, otic and nasal conditions by topically applying the compositions to the affected tissues. The compositions and methods of the invention are particularly useful in the treatment of acute otitis externa infections and ophthalmic infections attributable to one or both of two newly identified Microbacterium species, *Microbacterium otitidis* and *Microbacterium alconae*.

18 Claims, 1 Drawing Sheet

METHODS FOR TREATING OTIC AND OPHTHALMIC INFECTIONS

The present application is a continuation-in-part of U.S. application Ser. No. 09/575,850 filed May 19, 2000 now U.S. Pat. No. 6,509,327, which claims priority and is a continuation to: (1) International Application No. PCT/US99/22622 filed on Sep. 29, 1999, which claims priority based on U.S. Provisional Application Serial Nos. 60/102,504 and 60/102,506 filed on Sep. 30, 1998; (2) International Application No. PCT/US99/22624 filed on Sep. 29, 1999, which claims priority based on U.S. Provisional Application Serial Nos. 60/102,508 and 60/102,509 filed on Sep. 30, 1998; and (3) International Application No. PCT/US99/22625 filed on Sep. 29, 1999, which claims priority based on U.S. Provisional Application Serial Nos. 60/102,510 and 60/102,511 filed on Sep. 30, 1998.

BACKGROUND OF THE INVENTION

The present invention is directed to the provision of topical pharmaceutical compositions for treating otic infections, particularly acute otitis externa infections caused by two newly discovered bacterial species, Microbacterium sp. nov. *otitidis* and Microbacterium sp. nov. *alconae*. The present inventors have isolated these species, and have determined that these species are pathogens in acute otitis externa infections. The present invention is directed to the provision of topical pharmaceutical compositions and methods for treating otic infections that are partially or wholly attributable to these newly discovered bacterial species, as well as ophthalmic and nasal infections wherein these species are acting as pathogens. The compositions and methods of the present invention are based on the use of quinolone antibiotics to treat such infections, particularly second and third generation quinolones, such as gatifloxacin and moxifloxacin, respectively.

Quinolone antibiotics have been previously utilized to treat ophthalmic and otic infections. For example, a topical ophthalmic composition containing the quinolone ciprofloxacin is marketed by Alcon Laboratories, Inc. under the name CILOXAN™ (Ciprofloxacin 0.3%) Ophthalmic Solution, and a topical otic composition containing a combination of ciprofloxacin and hydrocortisone is marketed by Alcon Laboratories, Inc. under the name CIPRO™ HC. The following quinolones have also been utilized in ophthalmic antibiotic compositions:

| Quinolone | Product | Manufacturer |
| --- | --- | --- |
| Ofloxacin | OCUFLOX ™ | Allergan |
| Norfloxacin | CHIBROXIN ™ | Merck |
| Lomefloxacin | LOMEFLOX ™ | Senju |

Ofloxacin has also been utilized to treat otic infections.

The foregoing quinolone antibiotic compositions are generally effective in treating ophthalmic infections, and have distinct advantages over prior ophthalmic antibiotic compositions, particularly those having relatively limited spectrums of antimicrobial activity, such as: neomycin, polymyxin B, gentamicin and tobramycin, which are primarily useful against gram negative pathogens; and bacitracin, gramicidin, and erythromycin, which are primarily active against gram positive pathogens. However, despite the general efficacy of the ophthalmic quinolone therapies currently available, there is a need for improved compositions and methods of treatment based on the use of antibiotics that are more effective than existing antibiotics against key ophthalmic pathogens, and less prone to the development of resistance by those pathogens.

There is an even greater need for effective topical compositions and methods for treating otic and nasal infections, particularly bacterial infections. The use of oral antibiotics to treat otic infections in children has limited efficacy, and creates a serious risk of pathogen resistance to the orally administered antibiotics. Although ciprofloxacin has proven to be an effective agent in treating otic infections, there is a need for a better understanding of the etiology of these infections and a corresponding need for therapies that address the causes of these infections more directly and effectively.

Ophthalmic, otic and nasal infections are frequently accompanied by inflammation of the infected ophthalmic, otic and nasal tissues and perhaps even surrounding tissues. Similarly, ophthalmic, otic and nasal surgical procedures that create a risk of microbial infections frequently also cause inflammation of the affected tissues. Thus, there is also a need for ophthalmic, otic and nasal pharmaceutical compositions that combine the anti-infective activity of one or more antibiotics with the anti-inflammatory activity of one or more steroid or non-steroid agents in a single composition.

SUMMARY OF THE INVENTION

The invention is based on the use of a potent new class of antibiotics to treat ophthalmic, otic and nasal infections, as well as the use of these antibiotics prior to surgery to sterilize the surgical field and prophylactically following surgery or other trauma to otic, ophthalmic or nasal tissues to minimize the risk of infection. The compositions of the present invention may also be administered to the affected tissues during otic, ophthalmic or nasal surgical procedures to prevent or alleviate post-surgical infection. As utilized herein, the terms "treat", "treating" and derivations thereof are intended to include both treatments of existing infections and treatments to prevent or reduce the risk of infections.

The compositions preferably also contain one or more anti-inflammatory agents to treat inflammation associated with infections of otic, ophthalmic, or nasal tissues. The anti-inflammatory component of the compositions is also useful in treating inflammation associated with physical trauma to otic, ophthalmic, or nasal tissues, including inflammation resulting from surgical procedures. The compositions of the present invention are therefore particularly useful in treating inflammation associated with trauma to otic, ophthalmic, or nasal tissues wherein there is either an infection or a risk of an infection resulting from the trauma.

Examples of ophthalmic conditions that may be treated with the compositions of the present invention include conjunctivitis, keratitis, blepharitis, dacryocystitis, hordeolum and corneal ulcers. The compositions of the invention may also be used prophylactically in connection with various ophthalmic surgical procedures that create a risk of infection.

Examples of otic conditions that may be treated with the compositions of the present invention include otitis externa and otitis media. With respect to the treatment of otitis media, the compositions of the present invention are primarily useful in cases where the tympanic membrane has ruptured or tympanostomy tubes have been implanted. The compositions may also be used to treat infections associated with otic surgical procedures, such as tympanostomy, or to prevent such infections.

The compositions and methods of the present invention are particularly useful in the treatment of acute infections of the external ear canal, which are commonly referred to as "acute otitis externa" or "AOE". The present invention is based in part on the isolation of two bacterial species that have not previously been identified as pathogens relative to acute otitis externa infections. These bacterial species, which have been named "*Microbacterium otitidis*" and "*Microbacterium alconae*", are described in greater detail below. The present invention is also based in part on a finding that the quinolone antibiotics utilized in the present invention, particularly third generation quinolones, such as Moxifloxacin, have a very high level of antimicrobial activity against these newly discovered pathogens, and therefore are particularly useful in the treatment of acute otitis externa infections involving these pathogens.

The two bacterial species that have been identified as being associated with acute otitis externa infections have also been discovered to be associated with ophthalmic infections. As indicated above, the antibiotics utilized in the present invention have a high level of antimicrobial activity against these newly discovered ophthalmic pathogens, and as a result, the compositions of the present invention are particularly useful in treating ophthalmic infections involving these species.

The compositions of the present invention are specially formulated for topical application to otic, ophthalmic, and nasal tissues. The compositions are preferably sterile, and have physical properties (e.g., osmolality and pH) that are specially suited for application to otic, ophthalmic, and nasal tissues, including tissues that have been compromised as the result of preexisting disease, trauma, surgery or other physical conditions.

BRIEF DESCRIPTION OF THE DRAWING

The sole FIGURE of drawings is an automated ribotyping chart showing the relationships between two newly identified bacterial species and other, known species.

DETAILED DESCRIPTION OF THE INVENTION

Figure 1:
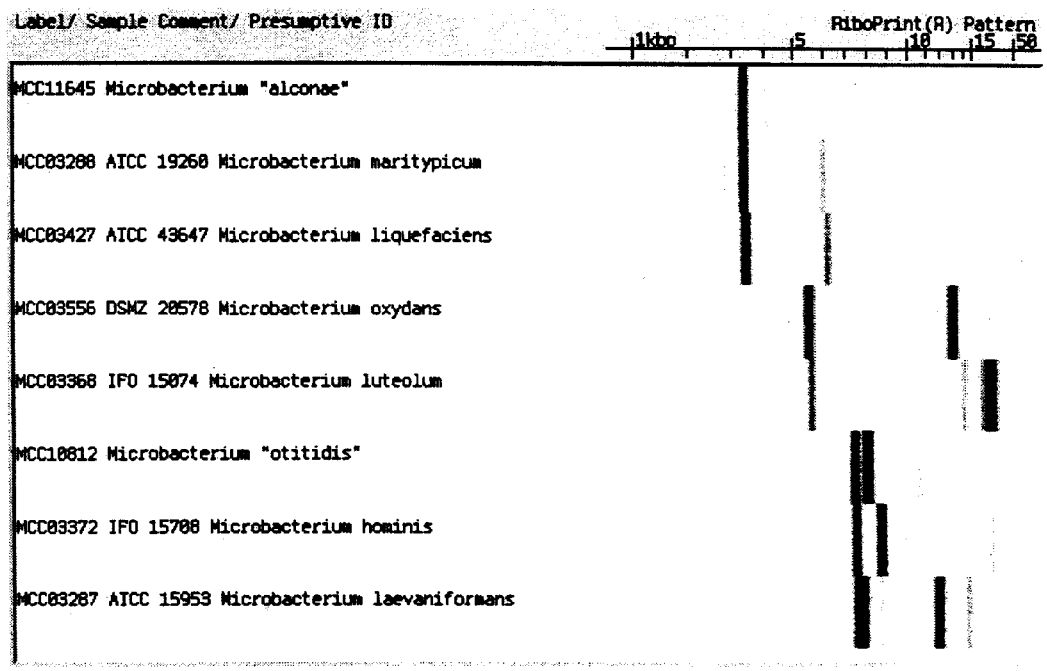

The antibiotics used in the compositions and methods of the present invention classified as quinolones. The preferred quinolones are second generation quinolones, such as Gatifloxacin, and third generation quinolones, such as Moxifloxacin. The designation of quinolone antibiotics as "second generation" or "third generation" is well known in the field of antibiotic therapy. This knowledge is reflected in numerous scientific articles, such as: Blondeau, J. M., "A review of the comparative in-vitro activities of 12 antimicrobial agents, with a focus on five new 'respiratory quinolones'", *J. of Antimicrobial Chemotherapy*, 43, Suppl. B. 1–11 (1999); Tillotson, G. S., "Quinolones: structure-activity relationships and future predictions", *J. of Medical Microbiology*, 44, 320-4 (1996); Wentland, M. P., "Structure-activity relationships of fluoroquinolones", *In the New Generation of Quinolones*, (Siporin, C., Heifetz, C. L. & Domagala, J. M., Eds), pp. 1–43, Marcel Dekker, New York (1990); and Gootz, T. D. and Brighty, K. E., "Fluoroquinolone antibacterials: SAR mechanism of action, resistance, and clinical aspects", *Medicinal Research Reviews* 16, 433–86 (1996). These articles provide further details regarding the structure/activity relationships of quinolone antibiotics and the classification of quinolones as second generation or third generation.

The preferred quinolone antibiotics are second generation quinolones, such as Ciprofloxacin, Ofloxacin, Gatifloxacin and Grepafloxacin, and third generation quinolones, such as Moxifloxacin and Trovafloxacin. The third generation quinolones are most preferred. Examples of second and third generation quinolones that may be utilized in the present invention are provided below.

The most preferred third generation quinolones are Moxifloxacin and related compounds of the following formula:

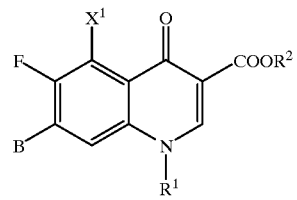

(I)

wherein:

A is CH, CF, CCl, C—OCH$_3$, or N;

X$^1$ is H, halogen, NH$_2$, or CH$_3$;

R$^1$ is C$_1$ to C$_3$ alkyl, FCH$_2$CH$_2$, cyclopropyl or phenyl, optionally mono-, di- or tri-substituted by halogen, or A and R$_1$ together can form a bridge of formula C—O—CH$_2$—CH(CH$_3$);

R$^2$ is H, C$_1$ to C$_3$ alkyl (optionally substituted by OH, halogen or NH$_2$), or 5-methyl-2-oxo-1,3-dioxol-4-yl-methyl; and B is a selected from the group consisting of:

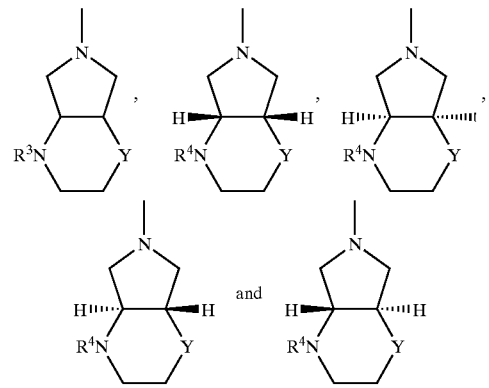

wherein:

Y is O or CH$_2$;

R$^3$ is C$_2$-C$_5$ alkoxyl, CH$_2$—CO—C$_6$H$_5$, CH$_2$CH$_2$CO$_2$R', R'O$_2$C—CH═C—CO$_2$R', CH═CH—CO$_2$R' or CH$_2$CH$_2$—CN, wherein:

R' is H or C$_1$ to C$_3$ alkyl;

R$^4$ is H, C$_1$ to C$_3$ alkyl, C$_2$-C$_5$ alkoxyl, CH$_2$—CO—C$_6$H$_5$, CH$_2$CH$_2$CO$_2$R', R'O$_2$C—CH═C—CO$_2$R', CH═CH—CO$_2$R', CH$_2$CH$_2$—CN or 5-methyl-2-oxo-1,3-dioxol-4-yl-methyl, wherein:

R' is H or C$_1$ to C$_3$ alkyl; and their pharmaceutically useful hydrates and salts.

The compound Moxifloxacin is most preferred. Moxifloxacin has the following structure:

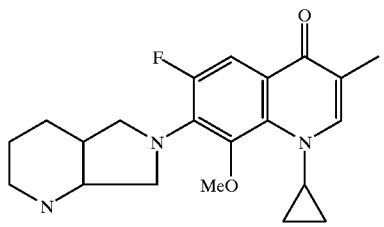

Further details regarding the structure, preparation, and physical properties of Moxifloxacin and other compounds of formula (I) are provided in U.S. Pat. No. 5,607,942. The contents of U.S. Pat. No. 5,607,942 relating to the structure, physical properties, and preparation of the compounds of formula (I) are hereby incorporated in the present specification by reference.

Other third generation quinolones that may be utilized in the present invention include Trovafloxacin and related compounds of the following formula:

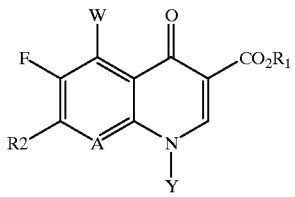

(II)

wherein
R1 is hydrogen, a pharmaceutically acceptable cation, or (C1–C6) alkyl;
Y, when taken independently, is ethyl, t-butyl, vinyl, cyclopropyl, 2-fluoroethyl, p-fluorophenyl, or o,p-difluorophenyl;
W is hydrogen, F, Cl, Br, C1–C4 alkyl, C1–C4 alkoxy, NH2 or NHCH3;
A is CH, CF, CCl, COCH3, C—CH3, C—CN or N; or
A is carbon and is taken together with Y and the carbon and nitrogen to which A and Y are attached to form a five or six membered ring which may contain oxygen or a double bond, and which may have attached thereto R8 which is methyl or methylene;
and
R2 is

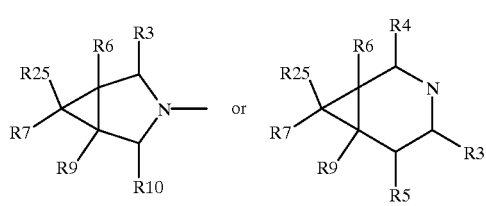

wherein:
R3, R4, R5, R6, R7, R9, R10 and R25 are each independently H, CH3, CH2NH2, CH2NHCH3 or CH2NHC2H5, and R5, R6, R7, and R9 may also independently be NH2, NHCH3 or NHC2H5, provided that not more than three of R3, R4, R5, R6, R7, R9, R10 and R25 are other than hydrogen, and if three of these substituents are not hydrogen, at least one of them is methyl.

The antibiotics utilized in the present invention also include prodrugs of the compounds of formula (II) having a free amino group, as well as pharmaceutically useful hydrates and salts of the compounds of formula (II).

The compound Trovafloxacin is most preferred. Trovafloxacin has the following structure:

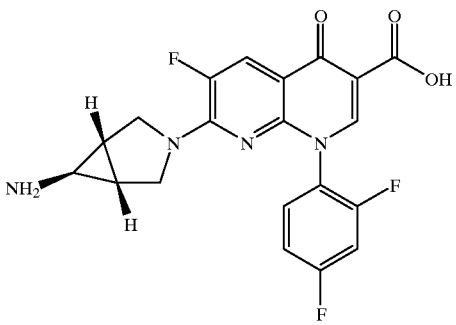

Further details regarding the structure, preparation, and physical properties of Trovafloxacin and other compounds of formula (II) are provided in U.S. Pat. No. 5,164,402. The contents of U.S. Pat. No. 5,164,402 relating to the structure, physical properties, and preparation of the compounds of formula (II) are hereby incorporated in the present specification by reference.

The second generation quinolones that may be utilized in the present invention include Gatifloxacin and related compounds of the following formula:

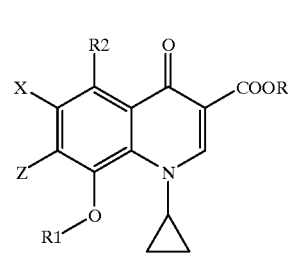

(III)

wherein R indicates a hydrogen atom or lower alkyl group, R1 indicates a lower alkyl group, R2 indicates a hydrogen atom X indicates a halogen atom, and Z indicates a halogen atom, piperazino group, N-methylpiperazino group, 3-methylpiperazino group, 3-hydroxypyrrolidino group, or pyrrolidino group of the following formula,

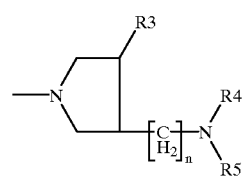

where, n is 0 or 1, R3 indicates a lower alkyl group, R4 indicates a hydrogen atom, lower alkyl group, hydroxy-substituted lower alkyl group or halogenated lower alkyl group and R5 indicates a hydrogen atom, lower alkyl group, acyl group or alkoxycarbonyl group, the hydrates or the pharmaceutically acceptable acid addition or alklai salts thereof.

The compound Gatifloxacin is most preferred. Gatifloxacin has the following structure:

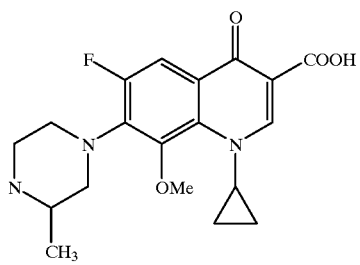

Further details regarding the structure, preparation, and physical properties of Gatifloxacin and other compounds of formula (III) are provided in U.S. Pat. No. 4,980,470. The contents of U.S. Pat. No. 4,980,470 relating to the structure, physical properties, and preparation of the compounds of formula (III) are hereby incorporated in the present specification by reference.

The second generation quinolones that may be utilized in the present invention also include Ciprofloxacin, Ofloxacin and Levofloxacin, as well as Grepafloxacin and related compounds of the following formula:

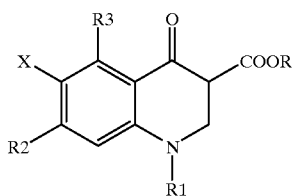

wherein

R1 is a cyclopropyl which may be substituted by 1 to 3 of substituents selected from the group consisting of a $C_1$–$C_6$ alkyl and a halogen atom, a phenyl which may be substituted by 1 to 3 of substituents selected from the group consisting of $C_1$–$C_6$ alkoxy, a halogen atom and hydroxy, a $C_1$–$C_6$ alkyl which may be substituted by a halogen atom, a $C_2$–$C_6$ alkanoyloxy or hydroxy, a $C_2$–$C_6$ alkenyl or thienyl;

R2 is a member selected from the group consisting of a 1-piperazinyl group which may have 1 to 3 substituents selected from the group consisting of a $C_1$–$C_6$ alkyl group, a $C_1$–$C_6$ alkanoyl group, a phenyl ($C_1$–$C_6$) alkyl group, and a 2-oxo-1,3-dioxolenemethyl group which may be substituted by a phenyl group or a $C_1$–$C_6$ alkyl group; a 1-pyrrolidinyl group which may have 1 to 3 substituents selected from the group consisting of an amino group which can have 1 or 2 substituents selected from a $C_1$–$C_6$ alkyl group and a ($C_1$–$C_6$)alkooxy-carbonyl group, an amino($C_1$–$C_6$)alkyl group which may have 1 to 2 substituents selected from $C_1$–$C_6$ alkyl group and a ($C_1$–$C_6$)alkoxy-carbonyl group on the amino moiety, and a $C_1$–$C_6$ alkyl group; a morpholino group which may have 1 to 3 substituents of $C_1$–$C_6$ alkyl groups; a 1-piperidinyl group which may have 1 to 3 substituents selected from the group consisting of a $C_1$–$C_6$ alkyl group, hydroxy, a halogen atom and oxo group; and a 1,4-diazobicyclo [4.3.0]nonan-4-yl group;

R3 is a $C_1$–$C_6$ alkyl;

R is hydrogen atom or a $C_1$–$C_6$ alkyl; and

X is a halogen atom, or a pharmaceutically acceptable salt thereof.

The compound Grepafloxacin has the following structure:

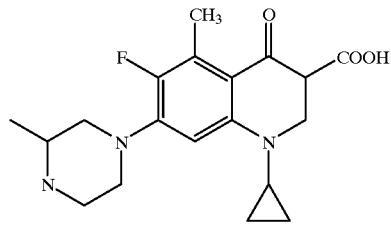

Further details regarding the structure, preparation, and physical properties of Grepafloxacin and other compounds of formula (IV) are provided in U.S. Pat. No. 5,563,138. The contents of U.S. Pat. No. 5,563,138 relating to the structure, physical properties, and preparation of the compounds of formula (IV) are hereby incorporated in the present specification by reference.

The concentrations of the antibiotics of formula (I) in the compositions of the present invention will vary depending on the intended use of the compositions (e.g., treatment of existing infections or prevention of post-surgical infections), and the relative antimicrobial activity of the specific antibiotic selected. The antimicrobial activity of antibiotics is generally expressed as the minimum concentration required to inhibit the growth of a specified pathogen. This concentration is also referred to as the "minimum inhibitory concentration" or "MIC". The term "$MIC_{90}$" refers to the minimum concentration of antibiotic required to inhibit the growth of ninety percent (90%) of the strains of a species. The concentration of an antibiotic required to totally kill a specified bacteria is referred to as the "minimum bactericidal concentration" or "MBC". The minimum inhibitory concentrations of Moxifloxacin, Trovafloxacin, Gatifloxacin and Grepafloxacin, relative to several bacteria commonly associated with otic, ophthalmic, and nasal infections, are provided in the following tables, wherein the concentrations are expressed as micrograms per milliliter:

| Microorganism | $MIC_{90}$ |
|---|---|
| Moxifloxacin | |
| S. aureus/methicillin sensitive | 0.13 |
| S. aureus/methicillin resistant | 4.0 |
| S. aureus/quinolone resistant | 4.0 |
| S. epidermidis/methicillin sensitive | 0.25 |
| S. epidermidis/methicillin resistant | 4.0 |
| S. pneumoniae/penicillin sensitive | 0.25 |
| S. pneumoniae/penicillin resistant | 0.25 |
| P. aeruginosa | 8.0 |
| H. influenzae/β-lactamase positive | 0.06 |
| H influenzae/β-lactamase negative | 0.06 |
| M. otitidis | 2.0 |
| M. alconae | 0.25 |
| Trovafloxacin | |
| S. aureus/methicillin sensitive | 0.03 |
| S. aureus/methicillin resistant | 2.0 |
| S. aureus/quinolone resistant | 4.0 |
| S. epidermidis/methicillin sensitive | 0.06 |
| S. epidermidis/methicillin resistant | 4.0 |
| S. pneumoniae/penicillin sensitive | 0.25 |
| S. pneumoniae/penicillin resistant | 0.25 |
| P. aeruginosa | 2.0 |
| H. influenzae/β-lactamase positive | 0.03 |
| H influenzae/β-lactamase negative | 0.03 |

-continued

| Microorganism | MIC$_{90}$ |
|---|---|
| Gatifloxacin | |
| S. aureus/methicillin sensitive | 0.25 |
| S. aureus/methicillin resistant | 8.0 |
| S. aureus/quinolone resistant | 8.0 |
| S. epidermidis/methicillin sensitive | 0.50 |
| S. epidermidis/methicillin resistant | 4.0 |
| S. pneumoniae/penicillin sensitive | 0.25 |
| S. pneumoniae/penicillin resistant | 0.25 |
| P. aeruginosa | 2.0 |
| H. influenzae/β-lactamase positive | 0.06 |
| H influenzae/β-lactamase negative | 0.06 |
| Grepafloxacin | |
| S. aureus/methicillin sensitive | 0.13 |
| S. aureus/methicillin resistant | 0.13 |
| S. aureus/quinolone resistant | 0.13 |
| S. epidermidis/methicillin sensitive | 0.13 |
| S. epidermidis/methicillin resistant | 0.13 |
| S. pneumoniae/penicillin sensitive | 0.25 |
| S. pneumoniae/penicillin resistant | 0.25 |
| P. aeruginosa | 8.0 |
| H. influenzae/β-lactamase positive | 0.008 |
| H influenzae/β-lactamase negative | 0.008 |

As indicated above, the present invention is based in part on the identification of two bacterial species that are believed to act as pathogens in acute otitis externa infections, *Microbacterium otitidis* and *Microbacterium alconae*. These bacteria belong to the class known as "coryneforms" or "diphtheroids". Bacteria belonging to this class have been previously identified as being present both in healthy ears and in ears afflicted with acute otitis externa infections. However, prior to the present invention, there had been no species-level identification of the coryneform bacteria present either in healthy ears or infected ears, nor had there been any attempt to eradicate the pathogenic species present in acute otitis externa infections with antibiotic therapy keyed to those species. The present inventors have now identified two species of coryneform bacteria as being present in acute otitis externa infections, and have determined that quinolone antibiotics, particularly third generation quinolones such as Moxifloxacin, are very effective in eradicating these species.

*Microbacterium otitidis* and *Microbacterium alconae* have also been discovered to be pathogens in infections of ophthalmic tissues, such as conjunctivitis and blepharitis. The compositions of the present invention are therefore particularly useful in treating ophthalmic infections involving one or both of these species.

The bacterial species referred to above were identified as a result of research conducted on specimens obtained from 2,122 ears afflicted with acute otitis externa infections and 82 healthy ears. Coryneform bacteria of some type were isolated from 10 to 30% of these ears overall; the incidence of finding this class of bacteria present varied depending on the season when the specimen was taken. Although coryneform bacteria have been identified previously in both healthy and infected ears, the present inventors have discovered that the coryneform bacteria present in healthy ears and in acute otitis externa ears are different. In the acute otitis externa ears, 80% of the coryneform bacteria identified belong to the genus Microbacterium, while in the healthy ears, 90% of the coryneform bacteria identified belong to the genus Turicella.

The present inventors have also discovered that the coryneform bacteria found in acute otitis externa patients include two species that have not previously been identified.

These species are now identified as Microbacterium sp. nov. *otitidis* and Microbacterium sp. nov. *alconae*. These names for the species have been assigned by the inventors, but have not yet been officially published. The names utilized for these species below are "*Microbacterium otitidis*" (sometimes abbreviated as "*M. otitidis*") and "*Microbacterium alconae*" (sometimes abbreviated as "*M. alconae*"), respectively.

In two thirds of the cases where *M. otitidis* or *M. alconae* isolates were identified as being present, these species were the only type of bacteria recovered. Moreover, these species were not recovered from healthy ears. These findings lead to the conclusion that *M. otitidis* and *M. alconae* are pathogens in acute otitis externa. That is, these species were either largely or totally responsible for the acute otitis externa infections in the ears from which they were isolated. The above-cited findings are believed to represent the first frequent association of the genus Microbacterium with a human infectious disease, namely, acute otitis externa. The two new Microbacterium species that have been discovered to be pathogens in acute otitis externa are described in greater detail below.

Both new species can be distinguished from the 27 recognized species of Microbacterium phenotypically and genotypically. Genotypically, *M. otitidis* is most closely related to *M. hominis*, while *M. alconae* is most closely related to *M. maritypicum* and *M. liquefaciens*.

The two new Microbacterium species have been characterized for taxomonic purposes using DNA methods as well as phenotypic methods. The sequencing of the 16S rRNA gene showed that both sets of strains belonged to the genus Microbacterium, although the sequence differences from established Microbacterium species were significant enough to suggest novel species. Automated ribotyping patterns further clarified the relationships (similarities and differences) with known Microbacterium species. These relationships are shown in FIG. 1. The above-cited analyses support the categorization of these bacteria as new species.

Both species of Microbacterium grow optimally at 28–30° C. The *M. otitidis* isolates grow up to 37° C., while the *M. alconae* isolates grow up to 35° C. The optimal growth temperature at 28–30° C. is typical for bacteria that are normally found in water and soil.

Phenotypically, the *M. otitidis* isolates are most easily distinguished from *M. hominis* by their inability to metabolize: 1)N-acetyl-D-glucosamine,2)3-methyl glucose, 3)alaninamide, or 4)L-serine. The isolates of *M. alconae* can be distinguished from *M. liquefaciens* by their ability to metabolize: 1) amygdalin,2)D-mannitol, 3) D-melezitose,4) palatinose, 5)D-psicose, 6)salicin, 7)D-sorbitol, 8)D-xylose, or 9) p-hydoxyphenyl acetic acid. Also, *M. alconae* can be distinguished from *M. maritypicum by their ability to metabolize:* 1)amygdalin or 2)D-xylose, and can be distinguished from *M. maritypicum* by their inability to metabolize: 1)L-fucose.

Analysis of cellular fatty acids for the *M. otitidis* isolates showed the three major fatty acids to be: 1)17:0 anteiso-60%,2)15:0 anteiso-26%, and 3)16:0 iso-11%. Analysis of the *M. alconae* isolates showed the three major fatty acids to be: 1)15:0 anteiso-55%,2)17:0 anteiso-23%,and 3)16:0 iso-11%.

The appropriate antibiotic concentration for ophthalmic compositions will generally be an amount of one or more antibiotics of formula (I) sufficient to provide a concentration in the aqueous humor and lacrimal fluid of the eye equal to or greater than the MIC$_{90}$ level for the selected antibiotic (s), relative to gram-negative and gram-positive organisms commonly associated with ophthalmic infections. The appropriate concentration for otic and nasal compositions will generally be an amount of one or more antibiotics of formula (I) sufficient to provide a concentration in the infected tissues equal to or greater than the MIC$_{90}$ level for the selected antibiotic(s), relative to gram-negative and gram-positive organisms commonly associated with otic or nasal infections. Such amounts are referred to herein as "an antimicrobial effective amount". The compositions of the present invention will typically contain one or more compounds of formula (I) in a concentration of from about 0.1 to about 1.0 percent by weight ("wt. %") of the compositions.

The compositions of the present invention may also contain one or more anti-inflammatory agents. The anti-inflammatory agents utilized in the present invention are broadly classified as steroidal or non-steroidal. The preferred steroidal anti-inflammatory agents are glucocorticoids.

The preferred glucocorticoids for ophthalmic and otic use include dexamethasone, loteprednol, rimexolone, prednisolone, fluorometholone, and hydrocortisone. The preferred glucocorticoids for nasal use include mometasone, fluticasone, beclomethasone, flunisolide, triamcinolone and budesonide.

The dexamethasone derivatives described in U.S. Pat. No. 5,223,493 (Boltralik) are also preferred steroidal anti-inflammatory agents, particularly with respect to compositions for treating ophthalmic inflammation. The following compounds are especially preferred:

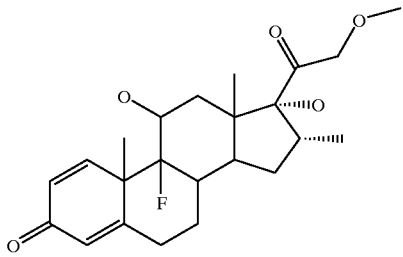

AL-1529

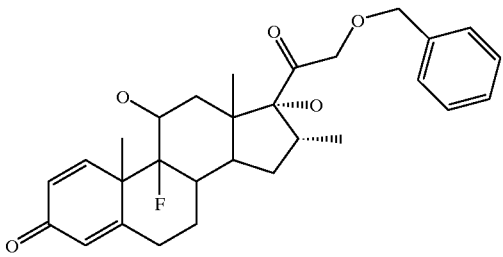

AL-2512

These compounds are referred to herein as "21-ether derivatives of dexamethasone". The 21-benzyl ether derivative (i.e., compound AL-2512) is particularly preferred.

The preferred non-steroidal anti-inflammatory agents are: prostaglandin H synthetase inhibitors (Cox I or Cox II), also referred to as cyclooxygenase type I and type II inhibitors, such as diclofenac, flurbiprofen, ketorolac, suprofen, nepafenac, amfenac, indomethacin, naproxen, ibuprofen, bromfenac, ketoprofen, meclofenamate, piroxicam, sulindac, mefanamic acid, diflusinal, oxaprozin, tolmetin, fenoprofen, benoxaprofen, nabumetome, etodolac, phenylbutazone, aspirin, oxyphenbutazone, NCX-4016, HCT-1026, NCX-284, NCX-456, tenoxicam and carprofen; cyclooxygenase type II selective inhibitors, such as NS-398, vioxx, celecoxib, P54, etodolac, L-804600 and S-33516; PAF antagonists, such as SR-27417, A-137491, ABT-299, apafant, bepafant, minopafant, E-6123, BN-50727, nupafant and modipafant; PDE IV inhibitors, such as ariflo, torbafylline, rolipram, filaminast, piclamilast, cipamfylline, CG-1088, V-11294A, CT-2820, PD-168787, CP-293121, DWP-205297, CP-220629, SH-636, BAY-19-8004, and roflumilast; inhibitors of cytokine production, such as inhibitors of the NFkB transcription factor; or other anti-inflammatory agents known to those skilled in the art.

The concentrations of the anti-inflammatory agents contained in the compositions of the present invention will vary based on the agent or agents selected and the type of inflammation being treated. The concentrations will be sufficient to reduce inflammation in the targeted ophthalmic, otic or nasal tissues following topical application of the compositions to those tissues. Such an amount is referred to herein as "an anti-inflammatory effective amount". The compositions of the present invention will typically contain one or more anti-inflammatory agents in an amount of from about 0.01 to about 1.0 wt. %.

The compositions are typically administered to the affected ophthalmic, otic or nasal tissues by topically applying one to four drops of a sterile solution or suspension, or a comparable amount of an ointment, gel or other solid or semisolid composition, one to four times per day. However, the compositions may also be formulated as irrigating solutions that are applied to the affected ophthalmic, otic or nasal tissues during surgical procedures.

The ophthalmic, otic and nasal compositions of the present invention will contain one or more compounds of formula (I) and preferably one or more anti-inflammatory agents, in pharmaceutically acceptable vehicles. The compositions will typically have a pH in the range of 4.5 to 8.0. The ophthalmic compositions must also be formulated to have osmotic values that are compatible with the aqueous humor of the eye and ophthalmic tissues. Such osmotic values will generally be in the range of from about 200 to about 400 milliosmoles per kilogram of water ("mOsm/kg"), but will preferably be about 300 mOsm/kg.

Ophthalmic, otic and nasal pharmaceutical products are typically packaged in multidose form. Preservatives are thus required to prevent microbial contamination during use. Suitable preservatives include: polyquaternium-1, benzalkonium chloride, thimerosal, chlorobutanol, methyl paraben, propyl paraben, phenylethyl alcohol, edetate disodium, sorbic acid, or other agents known to those skilled in the art. The use of polyquaternium-1 as the antimicrobial preservative is preferred. Typically such preservatives are employed at a level of from 0.001% to 1.0% by weight.

The solubility of the components of the present compositions may be enhanced by a surfactant or other appropriate co-solvent in the composition. Such co-solvents include polysorbate 20, 60, and 80, polyoxyethylene/polyoxypropylene surfactants (e.g., Pluronic F-68, F-84 and P-103), cyclodextrin, or other agents known to those skilled in the art. Typically such co-solvents are employed at a level of from 0.01% to 2% by weight.

The use of viscosity enhancing agents to provide the compositions of the invention with viscosities greater than the viscosity of simple aqueous solutions may be desirable to increase ocular absorption of the active compounds by the target tissues or increase the retention time in the eye, ear or nose. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents know to those skilled in the art. Such agents are typically employed at a level of from 0.01% to 2% by weight.

The following examples are provided to further illustrate the ophthalmic, otic and nasal compositions of the present invention.

Ophthalmic/Otic/Nasal Solution

| Ingredient | Amount (wt. %) |
|---|---|
| Moxifloxacin | 0.35 |
| Sodium Acetate | 0.03 |
| Acetic Acid | 0.04 |
| Mannitol | 4.60 |
| EDTA | 0.05 |
| Benzalkonium Chloride | 0.006 |
| Water | q.s. 100 |

Ophthalmic/Otic/Nasal Suspension

| Ingredient | Amount (wt. %) |
|---|---|
| Moxifloxacin | 0.3 |
| Dexamethasone, Micronized USP | 0.10 |
| Benzalkonium Chloride | 0.01 |
| Edetate Disodium, USP | 0.01 |
| Sodium Chloride, USP | 0.3 |
| Sodium Sulfate, USP | 1.2 |
| Tyloxapol, USP | 0.05 |
| Hydroxyethylcellulose | 0.25 |
| Sulfuric Acid and/or Sodium Hydroxide, NF | q.s. for pH adjustment to 5.5 |
| Purified Water, USP | q.s. to 100 |

Ophthalmic Ointment

| Ingredient | Amount (wt. %) |
|---|---|
| Moxifloxacin | 0.35 |
| Mineral Oil, USP | 2.0 |
| White petrolatium, USP | q.s 100 |

Ophthalmic Ointment

| Ingredient | Amount (wt. %) |
|---|---|
| Moxifloxacin | 0.3 |
| Fluorometholone Acetate, USP | 0.1 |
| Chlorobutanol, Anhydrous, NF | 0.5 |
| Mineral Oil, USP | 5 |
| White Petrolatum, USP | q.s. 100 |

The following example is provided to illustrate the activity of the compounds of formula (I) against the new Microbacterium species described above.

Example 5

The in vitro activity of Moxifloxacin against *Microbacterium otitidis* and *Microbacterium alconae* was determined using conventional agar and broth dilution methods, such as those described in NCCLS Document M7-A4, entitled "Methods for Dilution Antimicrobial Susceptability Tests for Bacteria That Grow Aerobically" ($4^{th}$ Edition). The activity levels were determined as MIC (minimum inhibitory concentration) values. In order to compare the activity of the compounds of the present invention to other antibiotics, MIC values for representatives quinolones, aminoglycosides, β-lactams and other types of antibiotics were also determined. The results of these determinations are set forth in the table below:

Activity of Moxifloxacin and Other Selected Antibiotics Against New Microbacterium Species

| | *Microbacterium otitidis* | | | | | *Microbacterium alconae* | | | | |
|---|---|---|---|---|---|---|---|---|---|---|
| Isolate Number→<br>Antibiotic ↓ | MCC 10647 | MCC 10810 | MCC 10990 | MCC 11495 | MCC 11676 | MCC 11316 | MCC 11558 | MCC 11639 | MCC 11653 | MCC 11699 |
| Quinolone | | | | | | | | | | |
| Ciprofloxacin | 32 | 32 | 32 | 32 | 32 | 1.0 | 1.0 | 1.0 | 2.0 | 2.0 |
| Moxifloxacin | 2.0 | 2.0 | 2.0 | 2.0 | 2.0 | 0.25 | 0.25 | 0.25 | 0.25 | 0.25 |
| Ofloxacin | 16 | 32 | 8.0 | 16 | 8.0 | 4.0 | 4.0 | 4.0 | 4.0 | 4.0 |
| Aminoglycosides | | | | | | | | | | |
| Tobramycin | 32 | 4.0 | 4.0 | 4.0 | 16 | 16 | 16 | 16 | 16 | 16 |
| Gentamicin | 8.0 | 4.0 | 4.0 | 16 | 4.0 | 2.0 | 2.0 | 2.0 | 2.0 | 2.0 |
| Neomycin | 8.0 | 2.0 | 2.0 | 8.0 | 2.0 | 1.0 | 1.0 | 1.0 | 1.0 | 1.0 |
| B-Lactams | | | | | | | | | | |
| Oxacillin | 2.0 | 4.0 | 2.0 | 4.0 | 2.0 | 8.0 | 16 | 32 | 32 | 32 |
| Other Antibiotics | | | | | | | | | | |
| Erythromycin | 0.03 | 0.03 | 0.03 | 0.03 | 0.03 | 1.0 | 2.0 | 2.0 | 0.50 | 0.50 |
| Clindamycin | 0.03 | 0.03 | 0.03 | 0.03 | 0.03 | 4.0 | 4.0 | 4.0 | 4.0 | 4.0 |
| Tetracycline | 1.0 | 1.0 | 1.0 | 1.0 | 1.0 | 1.0 | 1.0 | 1.0 | 1.0 | 1.0 |
| Chloramphenicol | 1.0 | 1.0 | 1.0 | 1.0 | 1.0 | 16 | 16 | 16 | 16 | 16 |
| Polymyxin B | 1040 | 260 | 260 | 1040 | 16 | 32.5 | 32.5 | 16 | 16 | 16 |

The letters "MCC" in the table above stand for "Microbiology Culture Collection". The MCC numbers (e.g., "MCC 10647") represent separate clinical isolates of the two Microbacterium species tested. The figures set forth in the table are the minimum inhibitory concentrations for each compound, relative to the respective isolates of the two Microbacterium species, expressed as micrograms per milliliter.

The invention has been described herein by reference to certain preferred embodiments. However, as obvious variations thereon will become apparent to those skilled in the art, the invention is not to be considered as limited thereto.

What is claimed is:

1. A method of treating otic infections or ophthalmic infections attributable to a Microbacterium species selected from the group consisting of *Microbacterium otitidis* and *Microbacterium alconae*, which comprises instilling a therapeutically effective amount of an antibiotic composition in the affected ear or eye to eradicate said pathogenic Microbacterium species, said composition comprising an antimicrobial effective amount of a quinolone antibiotic and a pharmaceutically acceptable vehicle therefor.

2. A method according to claim 1, wherein the antibiotic is selected from the group consisting of ciprofloxacin, ofloxacin, gatifloxacin, grepafloxacin, moxifloxacin and trovafloxacin.

3. A method according to claim 2, wherein said composition is instilled in the ear to treat acute otitis externa infections.

4. A method according to claim 2, wherein said composition is instilled in the eye to treat ophthalmic infections.

5. A method according to any one of claims 1–4, wherein the composition further comprises an effective amount of an anti-inflammatory compound.

6. A method according to claim 5, wherein the anti-inflammatory compound comprises a steroidal anti-inflammatory agent.

7. A method according to claim 6, wherein the steroidal anti-inflammatory agent comprises dexamethasone.

8. A method according to claim 5, wherein the anti-inflammatory compound comprises a non-steroidal anti-inflammatory agent.

9. A method according to claim 8, wherein the non-steroidal anti-inflammatory agent is a prostaglandin H synthetase inhibitor.

10. A method according to claim 9, wherein the non-steroidal anti-inflammatory agent comprises diclofenac.

11. A method according to claim 9, wherein the non-steroidal anti-inflammatory agent comprises nepafenac.

12. A method according to claim 9, wherein the non-steroidal anti-inflammatory agent comprises ketorolac.

13. A method according to claim 8, wherein the antibiotic comprises a third generation quinolone antibiotic.

14. A method according to claim 13, wherein the antibiotic comprises moxifloxacin.

15. A method according to claim 14, wherein the non-steroidal anti-inflammatory agent is a prostaglandin H synthetase inhibitor.

16. A method according to claim 14, wherein the non-steroidal anti-inflammatory agent comprises diclofenac.

17. A method according to claim 14, wherein the non-steroidal anti-inflammatory agent comprises nepafenac.

18. A method according to claim 14, wherein the non-steroidal anti-inflammatory agent comprises ketorolac.

* * * * *